US006410031B1

(12) United States Patent
Kwang et al.

(10) Patent No.: US 6,410,031 B1
(45) Date of Patent: Jun. 25, 2002

(54) ATTENTUATED PORCINE REPRODUCTIVE AND RESPIRATORY SYNDROME VIRUS STRAIN AND METHOD OF USE

(75) Inventors: Jimmy Kwang, Kentview Park (SG); Te Hung Chang, Tao-Yuan (TW)

(73) Assignee: Institute of Molecular Agrobiology (SG)

( * ) Notice: Subject to any disclaimer, the term of this patent is extended or adjusted under 35 U.S.C. 154(b) by 0 days.

(21) Appl. No.: 09/448,427

(22) Filed: Nov. 24, 1999

(30) Foreign Application Priority Data

Aug. 10, 1999 (SG) .............................................. 9903822

(51) Int. Cl.[7] .............................................. A61K 39/12
(52) U.S. Cl. .................. 424/218.1; 435/235; 435/236.1
(58) Field of Search .................... 424/218.1; 435/235.1, 435/236

(56) References Cited

PUBLICATIONS

Holland, J., et al., 1992, "RNA virus populations as quasispecies", Curr. Topics Microbiol. Immunol. 176:1–20.*
Steinhauer, D., and J. Holland, 1987, "Rapid Evolution of RNA viruses", Ann. Rev. Microbiol. 41:409–33.*
Morozov, I., et al., 1995, "Sequence analysis of open reading frames (ORFs) 2 to 4 of a U.S. isolate of porcine reproductive and respiratory syndrome virus", Arch. Virol. 140:1313–1319.*

* cited by examiner

*Primary Examiner*—Laurie Scheiner
*Assistant Examiner*—Jeffrey S. Parkin
(74) *Attorney, Agent, or Firm*—Rothwell, Figg, Ernst & Manbeck

(57) ABSTRACT

Porcine reproductive and respiratory syndrome (PRRS), which has also been termed mystery swine disease, swine infertility and respiratory syndrome (SIRS), and porcine epidemic abortion and respiratory syndrome (PEARS), induces severe disease in pigs and causes considerable economic loss to farmers. The pathology of PRRS is characterized by severe reproductive failure in sows, mild to severe respiratory distress, increased mortality in weaning pigs, conjunctivitis, and lymphnode enlargement. The pathogen responsible for PRRS is an enveloped RNA virus belonging to the Arterivirus group within the Togaviridae family. The PRRS viruses are single stranded RNA viruses having a viral genome of positive polarity and a size of approximately 15 kb. The positive-strand RNA genome possesses at least three major structural proteins designated N, M, and E. The PRRS viruses exist as a quasispecies and display considerable genotypic and phenotypic heterogeneity. The present invention is directed toward the isolation, characterization, and utilization of a novel PRRS viral isolate designated JK-100.

3 Claims, No Drawings

ATTENTUATED PORCINE REPRODUCTIVE AND RESPIRATORY SYNDROME VIRUS STRAIN AND METHOD OF USE

FIELD OF THE INVENTION

The present invention pertains to the discovery, isolation, characterization and utilization of a novel strain of porcine reproductive and respiratory syndrome (PRRS) virus. The invention further pertains to diagnostic and protective antigens and vaccines for the PRRS disease in pigs, and the methods of making and using the same.

BACKGROUND OF THE INVENTION

All publications and patent applications herein are incorporated by reference to the same extent as if each individual publication or patent application was specifically and individually indicated to be incorporated by reference.

Porcine reproductive and respiratory syndrome (PRRS) was first described in the United States in 1987 and in Germany in 1990. Other countries subsequently reporting the disease include France (1), Denmark (2), the Netherlands (3), Japan (4), Canada (5), Spain (6), and England (7). PRRS has the potential to become an economic disaster for U S. and European swine producers. There is evidence of extreme genetic and antigenic variability between American and European isolates (29).

This syndrome has variously been called mystery swine disease, swine infertility and respiratory syndrome (SIRS), abortus blau, blue eared pig disease, 'Lelystad virus',"Heko-heko" disease, and porcine epidemic abortion and respiratory syndrome (PEARS)(8–10).

The disease caused by the PRRS virus is characterized by: severe reproductive failure in sows, resulting in late term abortions with an inceased incidence of mummified, stillborn and weak pigs; chronic problems with delayed return to estrus; mild to severe respiratory distress, including sneezing, coughing, and nasal or ocular discharge in young pigs; increased mortality in preweaning, weaning and growing pigs; a mild flu-like disease in grower-finisher pigs; conjunctivitis, and lymph node enlargement (11–13). The respiratory syndrome is often associated with severe infection with secondary bacterial agents including *Pasteurella multocida, Haemophilus parasuis* and *Streptococcus suis* (8). Experimentally inoculated piglets showed clinical signs of depression, anorexia, pyrexia, diarrhea, sitting posture and periocular edema (12). One study estimated that the economic loss from PRRS on 91 Dutch farms averaged 29.5 kg per sow per year due to a decreased number of piglets raised per sow per litter, a prolonged farrowing interval and a higher replacement rate of sows (3).

The virus that is responsible for the disease is an enveloped RNA virus belonging to the Arterivirus group within the Togaviridae family. While data concerning morphology, morphogenesis and virion composition first suggested that the PRRS virus belonged to the Arterivirus group, this conclusion has been confirmed by analysis of genome organization, gene expression strategy and by comparison of deduced protein sequences. The arteriviruses also include the equine arteritis virus (EAV), lactate dehydrogenase elevating virus(LDV)and simian hemorrhagic fever virus (SHFV). The PRRS viruses are single stranded RNA viruses having a viral genome of positive polarity and a size of approximately 15 kb (15). These spherical virions are estimated to be 48–83 nm in diameter comprised of a 25–30 nm core surrounded by an envelope (3). The positive-strand RNA genome possesses at least three major structural proteins designated N, M, and E. The N protein is considered as the major component of the nucleocapsid, whereas M and E are membrane-associated (16). The nucleotide sequence of the genomic RNA of the PRRS virus has been determined for isolate CDI-NL-2.91 (Institut Pasteur deposit number I-1102) from overlapping cDNA clones (17). Eight open reading frames (ORFs) were identified in the consecutive sequence of 15,088 bp obtained for this isolate. The 3'-portion of the genome of another U.S. isolate, ATCCVR 2332, was also cloned and sequenced (18). The resultant 3,358 nucleotides contained 6 ORFs with homologies to ORFs 2 through 7 of the European strain of the PRRS virus and other members of the free-standing genus of arteriviruses.

As noted previously, there is evidence of extreme genetic and antigenic variability between different isolates of the PRRS virus. Thus, there is a need for the isolation, characterization, and utilization of novel PRRS viral isolates. Herein, we report on the discovery, isolation and use of the novel PRRS virus strain designated JK-100.

SUMMARY OF THE INVENTION

This invention comprises the identification and isolation of PRRS virus strains from selected piglets in infected herds, where the selected piglets showed signs of viremia and seroconversion but no clinical symptoms. More specifically, we have identified and isolated a novel PRRS viral strain designated JK-100.

The PRRS viral strain designated JK-100 has been deposited in accordance with the Budapest Treaty on the International Recognition of the Deposit of Microorganisms for the purpose of Patent Procedure with the China Center for Type Culture Collection, Wuhun University, Wuhun 430072, PRC, under the Designation CCTCC V 200005. The date of the deposit was Aug. 8, 2000.

The present invention also provides PRRS viral strains essentially corresponding to strain JK-100. The words "essentially corresponding" refer to variations that occur in nature and to artificial variations of JK-100, particularly those which still allow detection by techniques like hybridization, PCR and ELISA, using JK-100-specific materials, such as JK-100-specific antibodies.

The present invention provides for propagation of strain JK-100 to high titer in certain cell lines such as the MARC 145 cell line. This invention provides compositions of matter comprising the JK-100 strain. More specifically, this invention provides compositions of matter which comprise live, killed or attenuated JK-100 virus.

The present invention further provides a vaccine composition for vaccinating animals, in particular mammals, more particular pigs or swine, to protect them against PRRS disease. More specifically, the vaccine composition comprises the JK-100 viral strain, either live, killed, or attenuated; or an antigenic part or component of JK-100; a protein or antigenic polypeptide derived from, or a peptide mimicking an antigenic component of, JK-100; and a suitable carrier or adjuvant. Thus, the present invention also provides processes for preparing and using live virus or killed virus antigens (conventional or recombinant) and the vaccines resulting therefrom by combining an immunologically effective amount of the virus with diluent and/or adjuvant, respectively.

The invention also provides a diagnostic kit for detecting antigen from JK-100 in a sample, in particular a biological sample such as blood or blood serum, sputum, saliva, semen, or tissue, derived from an animal, in particular a mammal, more in particular a pig or swine, comprising an antibody which specifically recognizes a part or component of JK-100, and suitable detection means of an antigen detection assay. The invention further provides a diagnostic kit for detecting an antibody which specifically recognizes JK-100 in a sample, in particular a biological sample such as blood or blood serum, sputum, saliva, semen, or tissue, derived from an animal, in particular a mammal, more in particular a pig or swine, comprising JK-100; an antigenic part or component of JK-100; a protein or antigenic polypeptide derived from JK-100; or antigenic polypeptide derived from JK-100; or a peptide mimicking an antigenic component of JK-100; and suitable detection means of an antibody detection assay.

One skilled in the art can easily make any necessary adjustments in accordance with the necessities of the particular situation.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As set forth above, the present invention the isolation of the PRRS virus isolate JK-100 for the purpose of obtaining viral antigens for use in vaccines and diagnostic assays. Vaccination is the active immunization against the PRRS virus or its components, with the ultimate goal of protecting the host animal against subsequent challenge by the naturally occurring PRRS virus. The two broad classifications for viral vaccines are attenuated-live and noninfectious vaccines.

Noninfectious vaccines include inactivated "killed" virus vaccines, subunit vaccines, synthetic peptide and biosynthetic polypeptide vaccines, and anti-idiotype antibody vaccines. "Killed" or "dead" virus vaccines consist of virus particles whose infectivity has been destroyed by treatment with chemicals or radiation. Vaccines can simply be made by growing PRRS virus in pig lung macrophage cultures, or in other cell systems which support viral growth, and the virus, purified or not, can be killed by established techniques, such as inactivation with formaline or gamma (γ) radiation. The inactivated PRRS virus can then be combined with adjuvantia, such as Freund's adjuvant or aluminum hydroxide or others, and this composition can then be injected in pigs. These virus particles retain the ability to elicit an immune response and to protect from infection. Vaccines using even smaller components of the PRRS virus, such as polypeptides, peptides, or peptides mimicking antigenic components of the virus can also be used as dead vaccine.

An attenuated virus refers to any virus that has undergone attenuation by serial passage in cell culture or by other means. An attenuated vaccine is a live vaccine that contains organisms whose virulence for a host has been diminished or abolished. Attenuated vaccines are administered to produce an active immunity. Attenuating the virulence of a live virus by repeated passages in cells of species different than the natural host is one of the primary methods for developing attenuated-live virus vaccines. Attenuated vaccines against PRRS can be made by serially passaging the virus in pig lung macrophages, in lung macrophages of other species, or in other cell systems, or in other animals, such as rabbits, until it has lost its pathogenicity. Preferred non-host cells which can be used to produce attenuated PRRS include African Green Monkey Kidney cells (22) and MARC-145 cells (19). Live virus vaccines have been administered subdermally, subcutaneously, intramuscularly, intra nasally, orally, or by oropharyngeal aerosols.

Live or dead vaccines against PRRS can also be made by recombinant DNA techniques through which the genome of the virus, or parts thereof, is incorporated in vector systems such as vaccinia virus, herpesvirus, pseudorabies virus, adeno virus or other suitable vector systems that can so express the viral antigen. A recombinant vector could contain nucleic acid comprising a nucleotide sequence coding for a protein or antigenic peptide derived from PRRS virus; an antiqenic part or component of the virus; a protein or peptide mimicking an antigenic polypeptide derived from, or antigenic component of the virus; and a suitable carrier or adjuvant. Animals, in particular mammals, more in particular pigs or swine, vaccinated with such vector systems would then develop protective immune responses against PRRS.

Serological diagnosis of PRRS can be accomplished by testing serum or colostrum samples by art-known methods, including Immuno Peroxidase Monolayer Assay (IPMA), Immunofluorescent Antibody (IFA), Enzyme-Linked Immunosorbent Assay (ELISA), and Serum Virus Neutralization (SVN) test (23, 27, 30). Once infected animals have been identified, the PRRS virus can be isolated using methods well-known to those skilled in the art. The PRRS virus is then propagated to high titer, translating to high levels of antigenic mass, and its derivatives can be obtained by art-known means. For example, the antigenic mass can be obtained by dilution, concentration or extraction of the virus. Higher neutralizing antibody titers can be obtained by addition of either 10% or 20% guinea pig fresh serum to virus-serum mixtures in neutralizing tests (24, 25). It has also been demonstrated that complement-requiring neutralizing antibody titer increased in many serum samples when the virus-serum mixtures, rather than being incubated at 37 degrees C. for 60 minutes, were incubated first at 4 degrees C. for 24 hr or 48 hr and then with a complement at 37 degrees C. for 60 minutes (24, 25). Alternately, the protective antigens can be identified at the molecular level, reproduced and expressed through recombinant technology. Examples of the derivatives include subunit and recombinant forms thereof which are effective in accordance with the invention.

Subunit preparation can be developed as follows. Using a classical biochemical approach, viral proteins could be prepared from lysates of the host cells infected with PRRS virus. The infected cells are monitored for growth of the infectious agent by techniques such as IFA which detect antigen expression. With the purified preparation of PRRS virus in hand, one may exploit a host of recombinant DNA techniques directed toward developing subunits. The genetic material of the PRRS virus may be easily prepared by standard methods from lysates of cell cultures infected with PRRS virus. Genes that encode proteins identified as important immunogens, or that encode proteins likely to be immunogenic in the PRRS virus may be localized by using primers developed from consensus sequences and may then be subcloned into expression vectors of a type generally known to the art.

Such vectors may be expressed in cells or expressed in cell-free enzymatic transcription/translation systems. Antigenic proteins encoded by such vectors may be expressed and purified and, if properly post-translationally modified may be used immunogenically in accordance with the invention.

Genes identified as encoding immunogenic proteins may be amplified and purified for subcloning and DNA sequencing, using standard techniques known to the art. Isolated genes or gene fragments may, for example, be cloned directly into vectors or first be ligated to linkers having desirable restriction enzyme cut sites. DNA sequencing data obtained from cloned DNA fragments may be compared to known sequences, such as those of the Gen Bank repository, in an effort to identify the isolated organism and to more precisely explore the molecular biological bases of PRRS virus and the prevention of diseases caused thereby.

The aforementioned preparations require indicator reagents that identify antigenic proteins or that detect the presence of the PRRS virus in host cells. Such indicators may be obtained from polyclonal hyper immune sera isolated from swine that have been exposed to PRRS virus or by developing a battery of monoclonal antibodies directed against the intact PRRS virus. Monoclonal antibodies against the antigens of PRRS virus may produced by lysing the infected cells, purifying the PRRS virus from the lysates by gradient centrifugation, purifying its proteins and separating the proteins using SDS-PAGE electrophoresis. The SDS-PAGE gel may be stained using commassie blue or silver stain to obtain a profile of the PRRS virus proteins and carbohydrates. To determine which proteins are antigenic in pigs and, therefore, immunogens, a portion of the SDS-PAGE gel may be subjected to Western blot analysis using convalescent serum from PRRS virus infected pigs or using hyper immune sera. Transblotted proteins that are bound to serum antibodies may be visualized by sequential addition of an appropriate anti-antibody conjugate labeled with peroxidase and peroxidase-recognizing color substrate. A more precise determination of antigenic reactivity may be determined by subjecting protein fragments, rather than whole proteins, to SDS-PAGE electrophoresis.

A battery of monoclonal antibodies directed against specific proteins could then be raised by exercising from the SDS PAGE gel and injection into appropriate laboratory mice strains. B-cells isolated from an immunized mouse spleen could be fused with an immortalized cell line and screened to identify stable hybridomas that produce antibodies directed to the target protein.

To determine which antigenic epitopes are present on the surface of the PRRS virus, cells infected with PRRS virus may be harvested, purified by gradient centrifligation, and exposed to a battery of monoclonal antibodies raised against the PRRS virus. Then, a fluorescent-labeled anti-immunoglobulin can be applied to visualize the cell to which the monoclonal antibody has bound. Monoclonal antibodies directed particularly to surface antigens of the PRRS virus could then be grown in quantity and administered prophylactically to pig populations. For example, monoclonal antibodies have been produced against nucleocapsid proteins and a 19 kDa membrane protein of the virus (26, 28). One study found that no monoclonal antibodies produced from European isolates of the virus bound to U.S. isolates, indicating a consistent antigenic difference between the putative nucleocapsid of U.S. and European isolates (31).

Monoclonal and polyclonal antibodies with activity directed against surface antigens of the PRRS virus are useful not only as tools for selecting antigenic proteins created in vitro but also as possible therapeutic reagents in their own right. Presumably, antibodies directed against surface antigenic determinants of the PRRS virus, when administered to piglets, would passively immunize against PRRS virus.

Also, antibodies developed against the PRRS virus may be used in the field laboratory to monitor swine populations for the presence of PRRS virus using such assays as ELISA or EW estem blots to reveal the presence of a specific PRRS virus protein such as one carried on the surface of the PRRS virus, by binding to the protein an antibody that uniquely recognizes the protein. Such an approach would permit the certification of certain stocks as PRRS virus-free. Alternately, such an approach, when used a part of a routine pig screening program, could alert the grower to a developing problem in a seed stock population.

Materials and Methods

Isolation of the Virus

A blood sample was collected from an infected piglet which did not exhibit clinical signs of PRRS disease. The serum was filtered through a 0.45 micron filter and aliquoted into small volume prior to storage at −60° C.

One ml of serum was inoculated into a 75 cm$^2$ flask containing a fill monolayer of MARC-145 cells (19). The cell line had been grown in Eagle's minimum essential medium (MEM), supplemented with 10% fetal bovine serum and incubated at 37° C. (20). The inoculated culture was maintained in MEM with 5% fetal bovine serum and incubated at 32° C. The cells were observed daily for evidence of cytopathic effect (C2E).CPE was observed initially by the rounding of cells and a 70% detachment rate of the cells from the substrate 3–4 days post inoculation.

One ml of the medium was inoculated into another 75 cm$^2$ flask containing a full monolayer of MARC-145 cells. The remaining medium was aliquoted into small volumes and stored at −60° C.

The process was repeated five times. The titer obtained from the fifth passage was 5.5 log TCID $_{50}$/ml.

Test on embryonated eggs

Passage 5 field isolate (0.5 ml) was inoculated into 10 day-old embryonated chicken eggs and incubated for five days. The allantoic fluid of the inoculated eggs was further passaged twice through SPF chicken eggs. Hemagglutination test (HA) was carried out using the allantoic fluid from the third passage with chicken red blood cells (21).

The virus was found to be HA negative.

Test on porcine kidney cells

The PK15 cell line was grown in 25 cm$^2$ flask using Dulbecco's Modified Essential Medium (DMEM) supplemented with 10% fetal bovine serum.

The monolayer of cells was inoculated with 1 ml of the field isolate and maintained in DMEM with 5% fetal bovine serum at 37° C. The medium underwent blind passage twice using the same method (21).

The virus did not cause CPE on PK15 cells.

Subsequent Passage of the Virus

The virus was passaged further in the MARC-145 cell line until passage 20. The subsequent viral passages produced more pronounced CPE and attained a titer of 8.17 log TCID$_{50}$/ml by passage 20.

Each virus passage was titrated to determine the virus titrated to determine the virus titer and also tested by hnmunofluorescence Antibody assay (IFA) to verify the virus.

Immunofluorescence Assay

The field isolates were confirmed as PRRS virus by IFA with PRRS virus group specific monoclonal antibody, designated as SDOW 17(1) and polyclonal antiserum from infected pigs which showed clinical signs of PRRS disease.

MARC-145 cells were seeded into 96-well microplate and incubated overnight at 37° C. in a CO$_2$ incubator. Serial dilution of the viral isolate was carried out using MEM. The diluted virus was added into the wells and incubated for another 48 hours. The cells were fixed with absolute alcohol and air dried.

The monoclonal antibody from SDOW 17 and polyclonal serum from the pigs were used as the primary antibody for the assay. The secondary antibody used for SDOW 17 and pig serum was FITC-conjugated anti-mouse IgG and FITC-conjugated anti piq IgG respectively (11).

Florescence was confined to the cytoplasm of the cells, indicating the presence of the PRRS virus.

In vivo testing

The test was conducted in the laboratory using the virus from passage 20. Five 3-week-old piglets were inoculated with 6 log $TCID_{50}$ of virus. A control piglet was included the experiment. No symptoms of PRRS disease were observed in any piglets throughout the experiment.

Serum was collected three weeks later from the piglets for IFA. The test sera were tested together with monoclonal antibody from SDOW 17 and polyclonal antiserum from infected pigs which exhibited signs of PRRS disease.

The results show that the field isolate is PRRS virus does not produce the clinical signs of the disease in vivo.

Efficacy Trials

In order to show that viral strain JK-100 protects against PRRS, vaccination/challenge studies are conducted. Piglets, gilts and/or sows (hereinafter collectively referred to as "pigs") negative for antibody against PRRS are immunized with live or dead JK-100. Unimmunized pigs are housed separately and serve as controls. All of the pigs are tested for seroconversion. Vaccinated and control pigs next receive PRRS challenge virus. Food intake, rectal temperature and other clinical symptoms can be observed daily. Control pigs demonstrate signs of disease while no clinical signs of disease are noted in JK-100-exposed (vaccinated) pigs. Results of such vaccination/challenge studies demonstrate protection from clinical PRRS as a result of immunization with JK-100.

The foregoing detailed description has been given for clearness of understanding only and no unnecessary limitations should be understood therefrom as modifications will be obvious to those skilled in the art.

REFERENCES

Each of the following citations is herein incorporated by reference:

1. Baron T, Albina E, Leforban Y, Madec F, Guilmotot Ho, Plana Duran J, and Vannier P. Report on the first outbreaks of the porcine reproductive syndrome (PRRS) in France. Diagnosis and viral isolation. *Ann Rech Vet* 23(3):335 (1992).
2. Botner A, Nielsen J, and Bille-Hansen V. Isolation-of porcine reproductive and respiratory syndrome (PRRS) virus in a Danish swine herd and experimental infection of pregnant gilts with the virus. *Vet Microbiol* (*Netherlands*). 40(3–4):351–360 (1994).
3. Brouwer J, Frankena K, de Jong MF, Voets R, Dijkhuizen A, Verheijden J, and Komijn RE. PRRS: effect on herd performance after initial infection and risk analysis. *Vet O* (*Netherlands*) 16(2):95–100 (1994).
4. Murakami Y, Dato A, Tsuda T, Morozumi T, Miura Y, Sugimura T. Isolation and serological characterization of porcine reproductive and respiratory syndrome (PRRS) viruses from pigs with reproductive and respiratory disorders in Japan. *J Vet Med Sci* (*Japan*) 56(5):891–894 (1994).
5. Magar R, Larochelle, Dea S, Gagnon CA, Nelson EA,Christopher-Hennings J, Benfield DA. Antigenic comparison of Canadian and Us isolates of porcine reproductive and respiratory syndrome virus using monoclonal antibodies to the nucleocapsid protein. *Can J. Vet Res* (*Canada*) 59(3):232–234 (1995).
6. Suarez P., Zardoya R., Prieto C., Solana A., Tabares E., Bautista J. M., Castro J. M. Direct detection of the porcine reproductive and respiratory syndrome (PRRS) virus by reverse polymerase chain reaction (RT-PCR). *Arc Viron* (*Austria*)135(1–2):89–99 (1994).
7. Done S H and Paton D J. Porcine reproductive and respiratory syndrome: clinical disease pathology and immunosuppression. *Vet Rec* (*England*) 136(2):32–35 (1995).
8. Nelson E A, Hennings J C, Drew T, Wensvoort G, Collins J E and Benfield D A. Differentiation of U S and European Isolates of Porcine Reproductive and Respiratory Syndrome Virus by Monoclonal Antlbodies. *J Clin. Microbiol* 3184–3189 (1993).
9. Kuwahara H, Nunoya T, Tajima M, Kato A. Samejima T. An outbreak of porcine reproductive and respiratory syndrome in Japan. *J Vet Med Sci* (Japan)56(5):901–909 (1994).
10. Sanderson T., Mcginley M J, Zimmerman J J, Hill H T, Meetz M C, Pirtle E C, Swenson SL and Shibley GP. Porcine reproductive and respiratory syndrome virus antigen and processes for the preparation and use of said antigen in vaccines and diagnostics. U.S. Pat. No. 5,510,258. Date issued: Apr. 23, 1996.
11. Nelson E A, Hennings J C, and Benfield D A. Serum immune response to the proteins of porcine reproductive and respiratory syndrome (PRRS) virus. *J Vet Diagn Invest* 6:410–415 (1994).
12. Hirose O, Shibata I, Kudou H, Samegai Y, Yoshizawa S, Ono M, Nishimura M, Hiroike T, Kageyama K, and Sakano T. Experimental infection of SPF piglets with porcine reproductive and respiratory syndrome (PRRS) viruses isolated from two farms. *J. Vet Med Sci* (Japan) 57(6):991–1005 (1995).
13. Vezina S A, Loemba H, Fournier M, Dea S, and Archambault D. Antibody production and blastogenic response in pigs experimentally infected with porcine reproductive and respiratory syndrome virus. *Can J Vet Res* (Canada) 60(2):94–99 (1996).
14. Benfield D A, Nelson E, Collins J E, Harris L, Goyal S M, Robison D, Christianson W T, Morrison R B, Gorcyca D and Chladek D. Characterization of swine infertility and respiratory syndrome (SIRS) virus (isolate ATCC VR 2332). *J Vet Diagn Invest* 4:121–133 (1992).
15. Thiel H J, Meyers G, Stark R, Tautz N, Rumenapft, Unger G, and Conzelmann K K. Molecular characterization of positive-strand RNA viruses: pestiviruses and the porcine reproductive and respiratory syndrome virus (PRRSV). *Arch Virol Suppl* (Austria) 7:41–52 (1993).
16. Mardassi H, Massie B and Dea S. Intracellular synthesis, processing, and transport of proteins encoded by ORFs 5 to 7 of porcine reproductive and respiratory syndrome virus. *Virology* (United States) 221(1):98–112 (1996).
17. Wensvoort G, Terpstra C, and Pol JMA. Causative agent of the mystery swine disease, vaccine compositions and diagnostic kits. U.S. Pat. No. 5,620,691. Date issued: Apr. 15, 1997.
18. Murtaugh M P, Elam M R and Kakach L T. Comparison of the structural protein coding sequences of 18. the VR-2332 and Lelystad virus strains of the PRRS virus. *Arch Virol* (Austria) 140(8):1451–1460 (1995).
19. Stevenson G W, Van Alstine W G and Kanltz C L. Characterization of infection with endemic porcine reproductive and respiratory syndrome virus in a swine herd. *JAVMA* 204:1938–1942 (1994).
20. Kim H S, Kwang J. Yoon I J, Joo H S and Frey M L. Enhanced replication of porcine reproductive and respiratory syndrome (PRRS) in a homogeneous subpopulation of MA-104 cell line. *Arch Virol* 133:477–483 (1993).
21. Wensvoort G, Terpstra C, Pol JMA, ter Laak E A, Bloemraad M, de Kluyer E P, Kragten C, van Buiten L, den Besten A, Wagenaar F, Broekhuijsen J M, Moonen PLJM, Zestra T, de Boer E A, Tibben J H, de Jong M F, van't Veld P, Groenland G J R, van Gennep J A, Voets Mth, Verheijden J H M, Braamskamp J. Mystery swine disease in the Netherlands: the isolation of Leystad virus. *Vet 0* 13:121–130 (1991).
22. Sanderson T., Mcginley M J, Zimmerman J J, Hill H T, Meetz M C, M C, Pirtle E C, Swenson S L and Shibley G P. Porclne reproductive and respiratory syndrome virus antigen and processes for the preparation and use of said antigen in vaccines and diagnostics. U.S. Pat. No. 5,587,164. Date issued: Dec. 24, 1996.
23. Eichhom G. and Frost, J W. Study on the suitability of sow colostrum for the serological diagnosis of porcine reproductive and respiratory syndrome (PRRS). *Zentralbl Veterinarmed* (Germany) 44(2):65–72 (1997)
24. Takikawa N, Kobayashi S, Ide S, Yamane Y, Tanaka Y, Higashihara M and Yamagishi H. Early serodiagnosis of porcine reproductive and respiratory syndrome virus infection of pigs by detection of slow-reacting and complement-requiring neutralizing antibody. *J Vet Med Sci* (Japan) 59(1):31–34 (1997).
25. Jusa ER, Inaba Y, Kouno M, Hirose O, Shibata I, Kubota M, Yasuhara H. Slow-reacting and complement-requiring neutralizing antibody in swine infected with porcine reproductive and respiratory syndrome (PRRS) virus. *J Vet Med Sci* (Japan) 58(8):749–753 (1996).
26. Magar R, Larochelle R, Nelson E A and Charreyre C. Differential reactivity of a monoclonal antibodydirected to the membrane protein of porcine reproductive and respiratory syndrome virus. *Can J Vet Res* (Canada) 61(1):69–71 (1997).
27. Takikawa N, Kobayshi S, Ide S, Yamane Y, Tanaka Y and Yaniagishi H. Detection of antibodies against porcine reproductive and respiratory syndrome (PRRS) virus in swine sera by enzyme-linked immunosorbent assay. *J Vet Med Sci* (Japan) 58(4):355–357 (1996).
28. Mardassi H, Athanassious R, Mounir S and Dea S. Porcine reproductive and respiratory syndrome virus: morphological, biochemical and serological characteristics of Quebec isolates associated with acute and chronic outbreaks of porcine reproductive and respiratory syndrome. *Can J Vet Res* (Canada) 58(1): 55 5 64 (1994).
29. Done S H, Paton D J and White M E. Porcine reproductive and respiratory syndrome (PRRS): a review, with emphasis on pathological, virological and diagnostic aspects. *Br Vet J* (England) 152(2):153–174 (1996).
30. Yoon K J, Zimmerman J J, Swenson S L, McGinley M J, Eernisse K A, Brevik A, Rhinehart L L, Frey M L, Hill H T and Platt K B. *J Vet Diagn Invest*(United States) 7(3):305–312 (1995).
31. Drew T W, Meulenberg J J, Sands J J and Paton D J. Production, characterization and reactivity of monoclonal antibodies to porcine reproductive and respiratory syndrome virus. *J Gen Virol* (England) 76(Pt6):1361–1369 (1995).

What is claimed is:

1. An isolated porcine reproductive and respiratory syndrome virus designated JK-100 and having CCTCC Designation No. CCTCC V 200005.

2. A composition of matter comprising the virus of claim 1 combined with an adjuvant.

3. A composition of matter in accordance with claim 2 wherein the virus is killed.

* * * * *